US009622766B2

(12) United States Patent
Voic

(10) Patent No.: US 9,622,766 B2
(45) Date of Patent: Apr. 18, 2017

(54) ULTRASONIC INSTRUMENT ASSEMBLY AND METHOD FOR MANUFACTURING SAME

(71) Applicant: MISONIX INCORPORATED, Farmingdale, NY (US)

(72) Inventor: Dan Voic, Cedar Grove, NJ (US)

(73) Assignee: MISONIX INCORPORATED, Farmingdale, NY (US)

( * ) Notice: Subject to any disclaimer, the term of this patent is extended or adjusted under 35 U.S.C. 154(b) by 707 days.

(21) Appl. No.: 13/973,711

(22) Filed: Aug. 22, 2013

(65) Prior Publication Data

US 2015/0057692 A1 Feb. 26, 2015

(51) Int. Cl.
*A61B 17/32* (2006.01)
*A61B 17/3207* (2006.01)

(52) U.S. Cl.
CPC ......... *A61B 17/320068* (2013.01); *A61B 17/320783* (2013.01); *A61B 2017/320072* (2013.01);
(Continued)

(58) Field of Classification Search
CPC .. A61B 17/320092; A61B 2017/320072; A61B 2017/320076; A61B 2017/320084; A61B 17/230068; A61B 17/3207; A61B 17/320725; A61B 17/32075; A61B 17/320708; A61B 17/320758;
(Continued)

(56) References Cited

U.S. PATENT DOCUMENTS 6,270,471 B1 * 8/2001 Hechel ............ A61B 17/22012
604/22
6,338,717 B1 1/2002 Ouchi
(Continued)

FOREIGN PATENT DOCUMENTS

WO WO 01/24715 A1 4/2001
WO WO 02/094103 A1 11/2002
WO WO 2010/083362 A2 7/2010

OTHER PUBLICATIONS

Misonix, BoneScalpel System with SonicOne Technology. 2010, p. 18-19, 55, BCM-SS, MXB-S1.

*Primary Examiner* — Jonathan Miles
(74) *Attorney, Agent, or Firm* — R. Neil Sudol; Henry D. Coleman

(57) ABSTRACT

An ultrasonic surgical instrument assembly has a base, a rigid probe shaft coupled at a proximal end to the base, a probe head at a distal end of the shaft, and a sheath having a rigid distal end portion surrounding the shaft. The shaft has a longitudinal axis and is operatively connectable to a source of ultrasonic vibrational energy. The head extends eccentrically in a transverse direction to one side of the shaft, the head having an operative tip or surface spaced laterally from the axis. The distal end portion of the sheath is provided in a side wall with an aperture, and the probe head is aligned with the aperture. The sheath is coupled at a proximal end to the base and is provided with a partially flexible section between the distal end portion of the sheath and the instrument assembly base, so that the distal end portion is pivotably deflectable transversely to the axis in response to a lateral force applied to the distal end portion, to enable an increased protrusion of the head through the aperture.

8 Claims, 4 Drawing Sheets

(52) U.S. Cl.
CPC .......... *A61B 2017/320084* (2013.01); *A61B 2017/320096* (2013.01); *A61B 2017/320791* (2013.01); *A61B 2217/007* (2013.01)

(58) Field of Classification Search
CPC  A61B 2017/320766; A61B 17/320783; A61B 2017/320791; A61B 2017/320096; A61F 9/00745; A61F 9/00763
USPC .......................................... 606/169; 604/22
See application file for complete search history.

(56) References Cited

U.S. PATENT DOCUMENTS

| | | | | |
|---|---|---|---|---|
| 6,648,839 | B2* | 11/2003 | Manna | A61B 17/320068 601/2 |
| 7,771,444 | B2* | 8/2010 | Patel | A61B 17/320758 606/159 |
| 8,109,958 | B1* | 2/2012 | Alleyne | A61B 17/025 606/170 |
| 8,784,440 | B2* | 7/2014 | Lee | A61B 17/320725 606/159 |
| 2008/0058775 | A1* | 3/2008 | Darian | A61B 17/320068 606/1 |
| 2011/0112563 | A1* | 5/2011 | To | A61B 17/320758 606/159 |
| 2011/0196398 | A1* | 8/2011 | Robertson | A61B 17/32002 606/169 |
| 2011/0196403 | A1* | 8/2011 | Robertson | A61B 17/320068 606/169 |
| 2011/0196404 | A1* | 8/2011 | Dietz | A61B 17/22004 606/169 |
| 2013/0096589 | A1* | 4/2013 | Spencer | A61B 17/320758 606/159 |

\* cited by examiner

ULTRASONIC INSTRUMENT ASSEMBLY AND METHOD FOR MANUFACTURING SAME

BACKGROUND OF THE INVENTION

This invention relates to an ultrasonic tool or instrument assembly, particularly for use in medical surgical procedures. This invention also relates to an associated surgical method utilizing the ultrasonic instrument assembly or tool.

Over the past 30 years, several ultrasonic tools have been invented which can be used to ablate or cut tissue in surgery. Such devices are disclosed by Wuchinich et al. in U.S. Pat. No. 4,223,676 and Idemoto et al in U.S. Pat. No. 5,188,102.

In practice, these surgical devices include a blunt tip hollow probe that vibrates at frequencies between 20 kc and 100 kc, with amplitudes up to 300 microns or more. Such devices ablate tissue by either producing cavitation bubbles which implode and disrupt cells, tissue compression and relaxation stresses (sometimes called the jackhammer effect) or by other forces such as micro streaming of bubbles in the tissue matrix. The effect is that the tissue becomes liquefied and separated. It then becomes emulsified with the irrigant solution. The resulting emulsion is then aspirated from the site. Bulk excision of tissue is possible by applying the energy around and under an unwanted tumor to separate it from the surrounding structure. The surgeon can then lift the tissue out using common tools such as forceps.

The probe or tube is excited by a transducer of either the piezoelectric or magnetostrictive type that transforms an alternating electrical signal within the frequencies indicated into a longitudinal or transverse vibration. When the probe is attached to the transducer, the two become a single element with series and parallel resonances. The designer will try to tailor the mechanical and electrical characteristics of these elements to provide the proper frequency of operation. Most of the time, the elements will have a long axis that is straight and has the tip truncated in a plane perpendicular to the long axis. This is done for simplicity and economic considerations. In almost all applications, whether medical or industrial, such an embodiment is practical and useful. However, in applications such as the debridement of burns, wounds, diabetic ulcers or ulcers induced by radiation treatments, the blunt straight probe has been shown to be less effective in removing the hard eschar buildup that occurs when the wound is healing. This eschar buildup must be removed so that the healthy tissue is exposed and allowed to close the wound to provide complete healing with minimal scar tissue formation. Also, the small diameter tip, since it is cannulated, has a small annular area with limits energy transmission into the wound. This extends the length of the procedure and causes operator fatigue and patient discomfort.

Ultrasonic ablation tools are recognized for their accuracy, reliability and ease of use. Ultrasonic bone cutting blades may be designed to facilitate the cutting of bone without damage to adjacent soft tissues. See U.S. Pat. No. 8,343,178. Existing ultrasonic bone ablation tools have an operative tip or end effector surface that is knurled to enable progressive removal of layers of bone tissue from a bone surface. The instrument is moved generally in parallel with a bone surface at an operative site with the knurled operative tip or surface in contact with the bone surface.

As in the use of other surgical instruments, care must be taken to contact only the target tissues particularly if the instrument is under power so that the ablation surface is active and ultrasonically vibrating.

OBJECTS OF THE INVENTION

An object of the present invention is to provide an improved ultrasonic surgical instrument assembly.

A more particular object of the present invention is to provide such an improved instrument assembly for use in bone ablation.

It is another more particular object of the present invention to provide such an improved instrument assembly with enhanced safety structure and function.

It is a further object of the present invention to provide such an improved ultrasonic surgical instrument assembly with irrigation and/or suction capability.

It is an additional object of the present invention to provide an improved ultrasonic surgical instrument assembly that may be used in shaving bone tissues.

Another object of the present invention is to provide an associated surgical method, particularly a method with enhanced safety technique.

These and other objects of the invention will be apparent from the drawings and descriptions herein. Although every object of the invention is attained in at least one embodiment of the invention, there is not necessarily any embodiment which attains all of the objects of the invention.

SUMMARY OF THE INVENTION

An ultrasonic surgical instrument assembly in accordance with the present invention comprises a rigid probe shaft couplable at a proximal end to a source of ultrasonic vibrational energy, a probe head at a distal end of the shaft, and a sheath having an at least semi-rigid distal end portion surrounding the shaft. The shaft has a longitudinal axis and the head extends eccentrically in a transverse direction to one side of the shaft. The head has an operative tip or surface spaced laterally from the axis. The distal end portion of the sheath is provided in a side wall with an aperture, and the probe head is aligned with the aperture. The sheath is partially flexible so that the distal end portion is pivotably deflectable transversely to the axis in response to a lateral force applied to the distal end portion, to enable an increased protrusion of the head through the aperture.

In a neutral or inactive state the instrument assembly has a configuration where the head is at least partially retracted into the sheath so that the operative tip or surface is approximately flush with the side wall of the sheath. Thus, in the neutral or inactive state of the instrument assembly, the probe head protrudes at most minimally from the sheath. In some instrument embodiments, the operative tip or surface may be disposed entirely within the sheath prior to a deflection of the distal end portion of the sheath.

Pursuant to another feature of the present invention, the shaft and the head are formed with a bore or channel having an outlet at the operative tip or surface. Optionally, the bore or channel may have another outlet at a distal end of the shaft, that additional outlet being proximate to the an auxiliary opening at the distal tip of the sheath.

The distal end portion of the sheath may be closed or open at the distal tip thereof.

Typically, the operative tip or surface is a knurled surface, particularly designed for removal of layers of hard tissues such as bone.

The probe head may be spaced from an edge of the aperture to form a gap for liquid egress from the sheath.

A surgical method in accordance with the present invention utilizes an ultrasonic surgical instrument assembly including a shaft with a head extending eccentrically to one the of the shaft, the instrument assembly further including a sheath surrounding the shaft and having a distal end portion with an aperture aligned with the head, the head being extendable through the aperture. The method comprises (a) moving the instrument assembly so that a side of the sheath comes into contact with tissues at an operative site, (b) pivotally deflecting the distal end portion of the sheath by virtue of a lateral pressure applied by the contact of the sheath with the tissues, (c) increasing a degree of protrusion of the head through the aperture by virtue of the deflecting of the distal end portion of the sheath, (d) contacting the tissues with an operative tip or surface of the head, and (e) ultrasonically vibrating the shaft and the head during contact of the operative tip or surface with the tissues.

The method has an ending phase wherein the instrument assembly is moved to terminate contact between the tissues and the distal end portion of the sheath, returning the distal end portion returns to a neutral or rest position and retracting the head at least partially into the sheath through the aperture. The returning of the distal end portion of the sheath to the neutral or rest position preferably occurs automatically owing to an internal spring contact of a flexible coupling between the distal end portion and a base or hand piece of the instrument assembly.

The method may further comprise feeding a liquid through the aperture during contact of the operative tip or surface with the tissues. The liquid may be fed through a gap between a defining edge of the aperture and the probe head and/or through a bore in the probe head communicating with a channel in the shaft.

DETAILED DESCRIPTION

Figure 1:
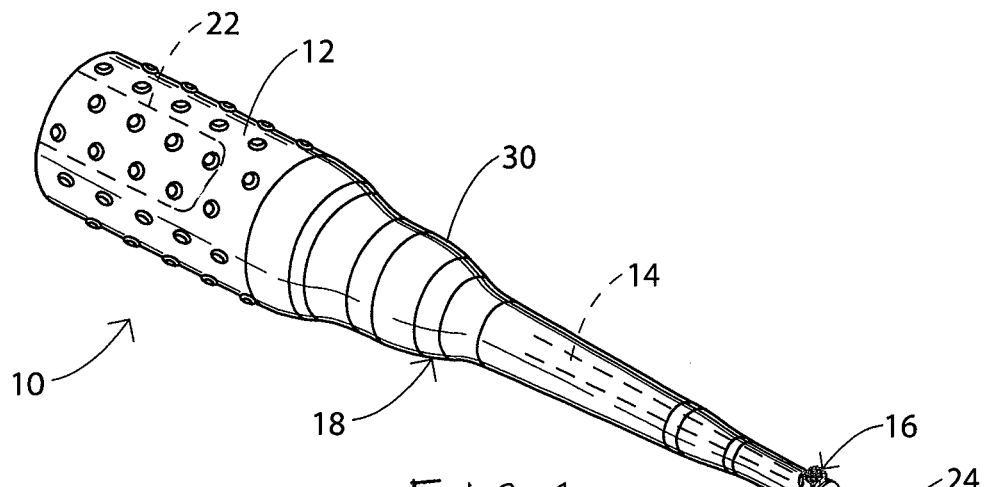
FIG. 1 is a schematic isometric view of an ultrasonic bone ablation instrument assembly in accordance with the present invention.
Figure 2:
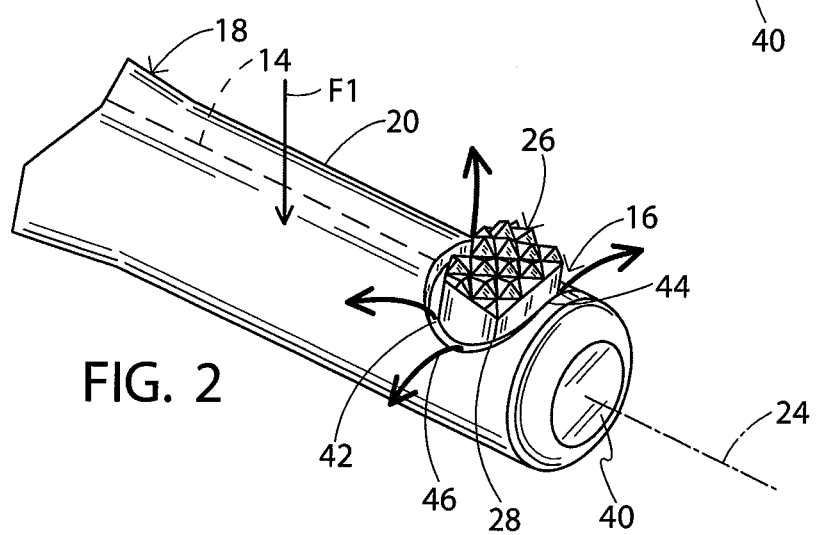
FIG. 2 is a schematic isometric view, on a larger scale, of a distal end portion of the ultrasonic bone ablation instrument assembly of FIG. 1.
Figure 3:
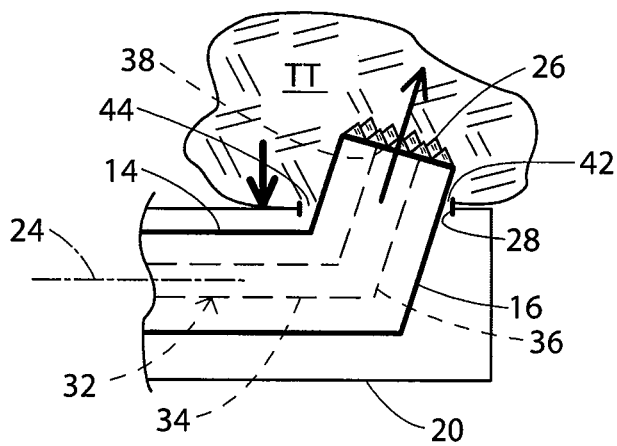
FIG. 3 is a diagram of a longitudinal cross-section of the distal end portion of the ultrasonic bone ablation instrument assembly of FIGS. 1 and 2.

As depicted in FIGS. 1-3, an ultrasonic surgical instrument assembly 10 comprises a sheath 18 that has an at least semi-rigid distal end portion 20 and a base or enlarged proximal end portion 12. Base 12 fits over a nose portion 208 of a transducer-carrying handpiece 206, as discussed hereinafter with reference to FIG. 7-10.

Instrument assembly 10 further comprises a rigid probe shaft 14 that may be coupled at a proximal end to a piezoelectric or magnetostrictive transducer 22 in the handpiece 206. Probe shaft 14 is provided at a distal end with a probe head 16.

Shaft 14 has a longitudinal axis 24, while head 16 extends eccentrically in a transverse direction to one side of the shaft. Head 16 has an operative tip or surface 26 spaced laterally from axis 24. Tip or surface 26 is knurled for hard-tissue ablation purposes.

Distal end portion 20 of sheath 18 is provided in a side wall (not separated enumerated) with an aperture 28, probe head 16 being aligned with and extendable through the aperture. Distal end portion 20 of sheath 18 is movable in a transverse direction so that head 16 protrudes to a variable extent through aperture 28. Sheath 18 is coupled at a proximal end to base 12 and is provided with a flexible section 30 anywhere between distal end portion 20 and base 12, so that the distal end portion of the sheath is pivotally deflectable transversely to axis 24 in response to a lateral force F1 applied to distal end portion 20. The deflection or movement of sheath 18 towards shaft 14 enables an increased protrusion of head 16 through aperture 28.

In a neutral or inactive state, instrument assembly 10 has a configuration where head 16 is at least partially retracted into sheath 18. In the neutral or inactive state of instrument assembly 10, probe head 16 protrudes at most minimally from sheath 18 and operative tip or surface 26 may be approximately flush with the side wall of the sheath. In some instrument embodiments, the operative tip or surface 26 may be disposed entirely within sheath 18 prior to a deflection of the distal end portion 20 of the sheath.

Shaft 14 and head 16 may be formed with a bore or channel 32 having an axial segment 34 in shaft 14 and a transverse segment 36 in head 16, with an outlet 38 at the operative tip or surface 26. A distal tip 40 of sheath 18 is closed.

Probe head 16 is spaced from an edge 42 of aperture 28 to form a gap 44 for liquid egress 46 from sheath 18.

Figure 4:
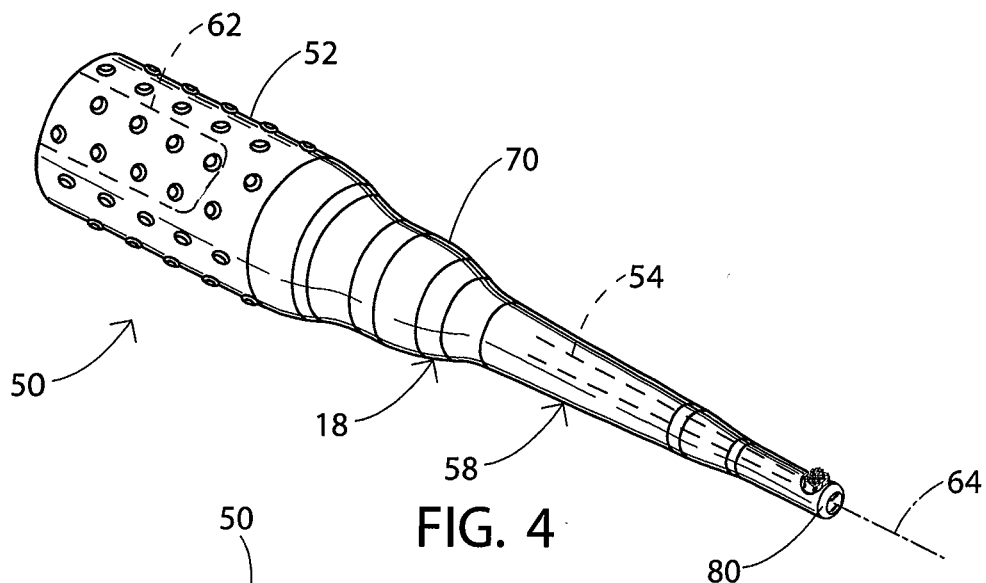
FIG. 4 is a schematic isometric view of a modified embodiment of an ultrasonic bone ablation instrument assembly in accordance with the present invention.
Figure 5:
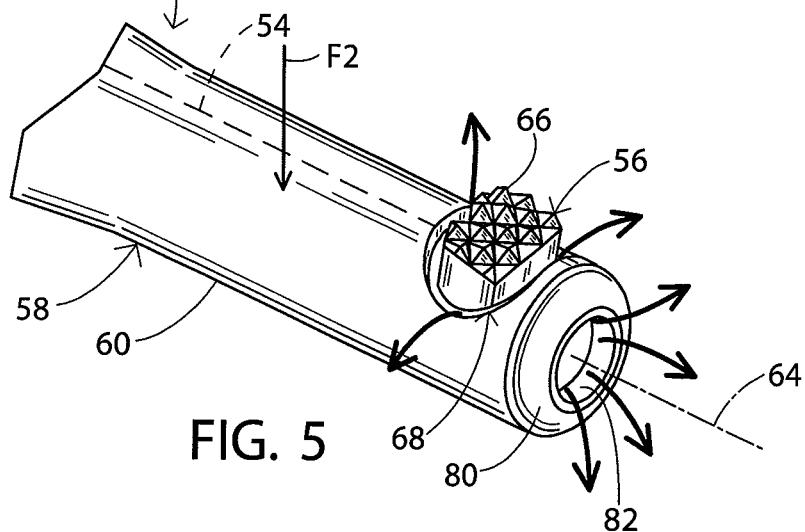
FIG. 5 is a schematic isometric view, on a larger scale, of a distal end portion of the ultrasonic bone ablation instrument assembly of FIG. 4.
Figure 6:
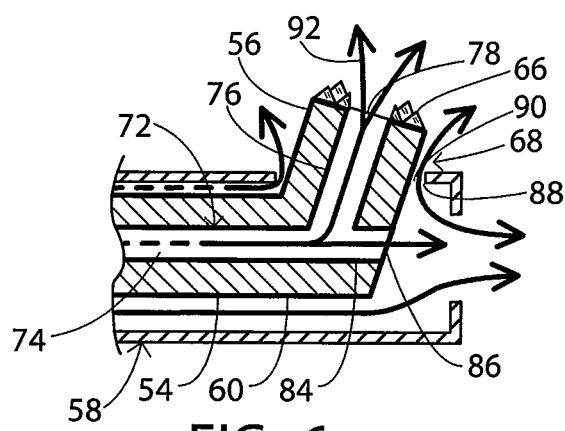
FIG. 6 is a diagram of a longitudinal cross-section of the distal end portion of the ultrasonic bone ablation instrument assembly of FIGS. 4 and 5.
Figure 7:
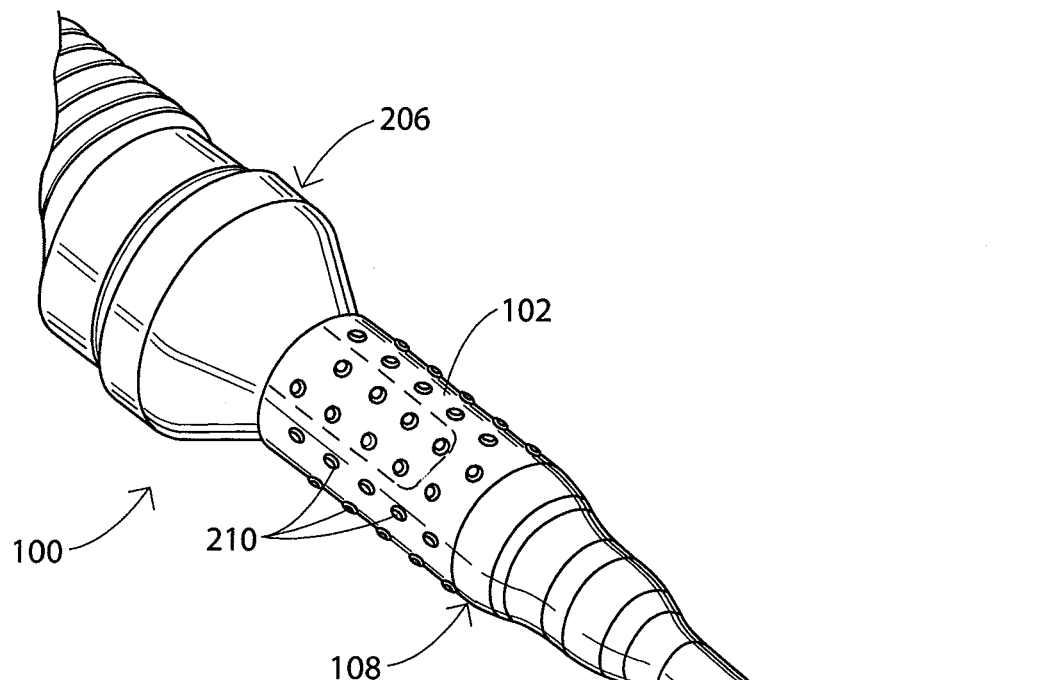
FIG. 7 is a schematic isometric view of another embodiment of an ultrasonic bone ablation instrument assembly in accordance with the present invention.
Figure 8:
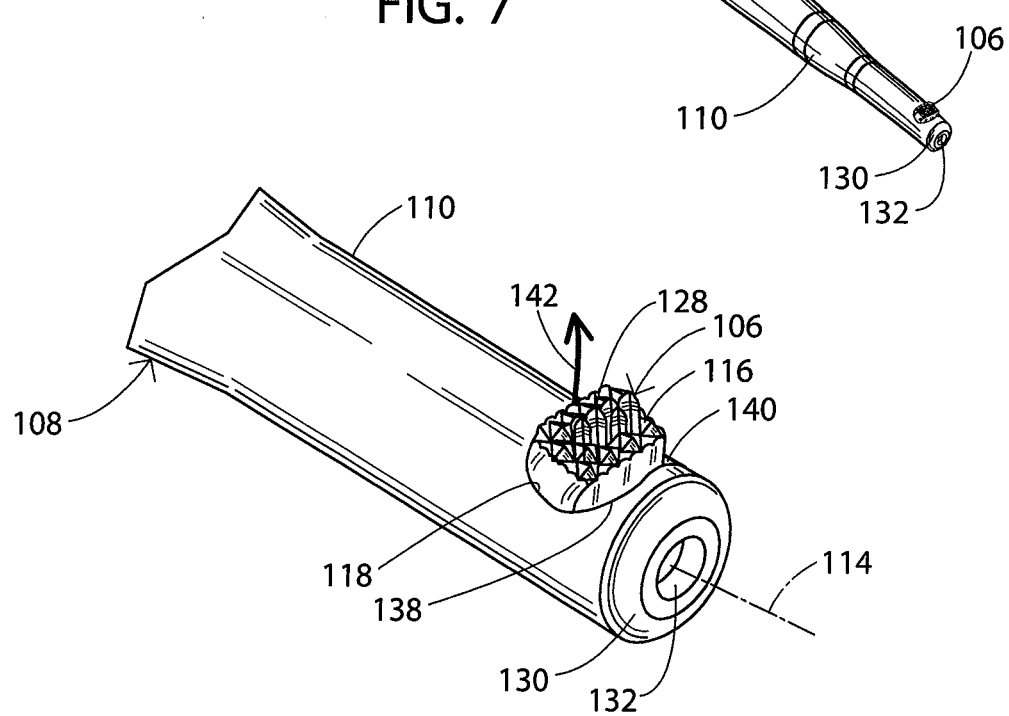
FIG. 8 is a schematic isometric view, on a larger scale, of a distal end portion of the ultrasonic bone ablation instrument assembly of FIG. 7.
Figure 9:
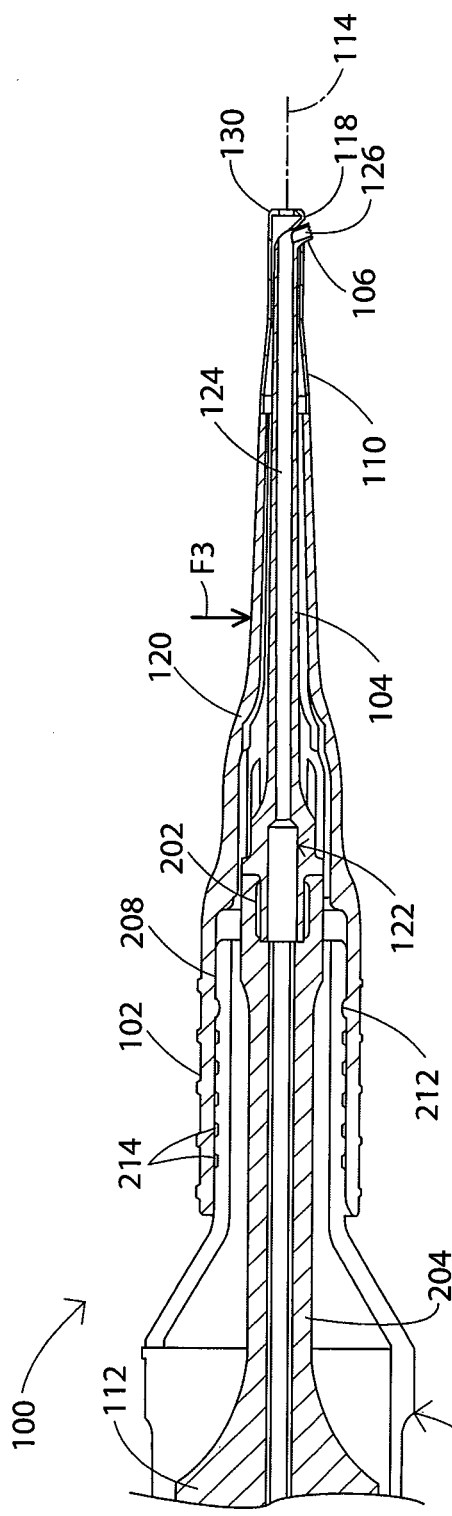
FIG. 9 is a schematic longitudinal cross-section of the ultrasonic bone ablation instrument assembly of FIGS. 7 and 8.
Figure 10:
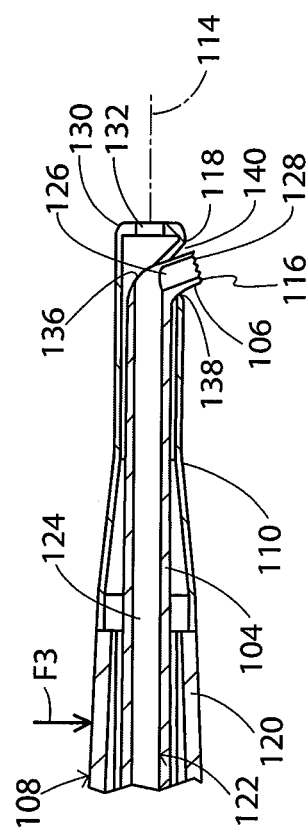
FIG. 10 is a schematic longitudinal cross-sectional view, on a larger scale, of the distal end portion of the ultrasonic bone ablation instrument assembly of FIGS. 7-9.

As depicted in FIGS. 4-6, an ultrasonic surgical instrument assembly 50 comprises a sheath 58 that has an at least semi-rigid distal end portion 60 and a base or enlarged proximal end portion 52. Base 52 fits over a nose portion 208 of a transducer-carrying handpiece 206 (see FIG. 7-10).

Instrument assembly 50 further comprises a rigid probe shaft 54 that may be coupled at a proximal end to a piezoelectric or magnetostrictive transducer 62 in the handpiece 206. Probe shaft 54 is provided at a distal end with a probe head 56.

Shaft 54 has a longitudinal axis 64, while head 56 extends eccentrically in a transverse direction to one side of the shaft. Head 56 has an operative tip or surface 66 spaced laterally from axis 64. Tip or surface 66 is knurled for hard-tissue ablation purposes.

Distal end portion 60 of sheath 58 is provided in a side wall (not separated enumerated) with an aperture 68, probe head 56 being aligned with and extendable through the aperture. Distal end portion 60 of sheath 58 is movable in a transverse direction so that head 56 protrudes to a variable extent through aperture 68. Sheath 58 is coupled at a proximal end to base 52 and is provided with a flexible section 70 between distal end portion 60 and base 52, so that the distal end portion of the sheath is pivotally deflectable transversely to axis 64 in response to a lateral force F2 applied to distal end portion 60. The deflection or movement of sheath 58 towards shaft 54 enables an increased protrusion of head 56 through aperture 68.

In a neutral or inactive state, instrument assembly 50 has a configuration where head 56 is at least partially retracted into sheath 58. In the neutral or inactive state of instrument assembly 50, probe head 56 protrudes minimally from sheath 58 and operative tip or surface 66 may be approximately flush with the side wall of the sheath. In some instrument embodiments, the operative tip or surface 66 may be disposed entirely within sheath 58 prior to a deflection of the distal end portion 60 of the sheath.

Shaft 54 and head 56 may be formed with a bore or channel 72 having an axial segment 74 in shaft 54 and a transverse segment 76 in head 56, with an outlet 78 at the operative tip or surface 66. A distal tip 80 of sheath 58 is provided with an opening 82. Bore or channel segment 74 has an axial extension 84 ending in an auxiliary fluid outlet 86 proximate to and aligned with opening 82.

Probe head 56 is spaced from an edge 88 of aperture 68 to form a gap 90 for liquid egress 92 from sheath 58.

As depicted in FIGS. 7-10, another ultrasonic surgical instrument assembly 100 comprises a sheath or sleeve 108 and a rigid probe shaft 104. Probe shaft 104 is operatively coupled at a proximal end via a screw thread coupling 202 to a front driver 204 of a piezoelectric or magnetostrictive transducer assembly 112 disposed in a handpiece 206. Probe shaft 104 is formed at a distal end with an eccentrically extending probe head 106.

Sheath or sleeve 108 has a base or proximal end portion 102 of enlarged diameter that is fitted over and mounted to a nose portion 208 of handpiece 206. Proximal sheath portion 102 is formed on an exterior surface with a cylindrical array of protrusions or nubs 210 and provided on an inner surface with at least one projection 212 such as a cylindrical rib or one or more nubs. Projection 212 is received in one of a plurality of recesses or grooves 214 on an external surface of nose portion 208, enabling an adjustment in the degree of extension of sheath 108 from handpiece 206.

Sheath 108 includes a substantially rigid distal end portion 110 which surrounds probe shaft 104. Shaft 104 has a longitudinal axis 114, while probe head 106 extends eccentrically in a transverse direction to one side of the shaft. Head 106 has an operative tip or surface 116 spaced laterally from axis 114. Tip or surface 116 is knurled for hard-tissue ablation purposes.

Distal end portion 110 of sheath 108 is provided in a side wall (not separated enumerated) with an aperture 118, probe head 106 being aligned with and extendable through the aperture. Distal end portion 110 of sheath 108 is movable in a transverse direction so that head 106 protrudes to a variable extent through aperture 118. Sheath 108 includes a partially flexible semi-rigid middle section 120 between distal end portion 110 and enlarged proximal portion 102, so that the distal end portion of the sheath is pivotally deflectable transversely to axis 114 in response to a lateral force F3 applied to sheath 108. The deflection or movement of sheath 108 towards shaft 114 enables an increased protrusion of head 106 through aperture 118.

In a neutral or inactive state, instrument assembly 100 has a configuration where head 106 is at least partially retracted into sheath 108. In the neutral or inactive state of instrument assembly 100, probe head 106 protrudes minimally from sheath 108 and operative tip or surface 116 may be approximately flush with the side wall of the sheath. In some instrument embodiments, the operative tip or surface 116 may be disposed entirely within sheath 108 prior to a deflection of the distal end portion 110 of the sheath.

Probe shaft 104 and head 106 may be formed with a bore or channel 122 having an axial segment 124 in shaft 104 and a transverse segment 126 in head 106, with an outlet 128 at the operative tip or surface 116. A distal tip 130 of sheath 108 is provided with an opening 132. Bore or channel segment 124 has an auxiliary fluid outlet 136 proximate to and aligned with opening 132.

Probe head 106 is spaced from an edge 138 of aperture 118 to form a gap 140 for liquid egress 142 from sheath 108.

In a surgical method utilizing ultrasonic surgical instrument assembly 10, 50 or 100, one moves the instrument so that a side or lateral surface of sheath 18, 58, 108 comes into contact with tissues TT (FIG. 3) at an operative site. The contact pressure F1, F2, F3 is sufficient to pivotally deflect the distal end portion 20, 60, 110 of sheath 18, 58, 108 toward axis 24, 64, 114, thereby increasing an amount of protrusion of probe head 16, 56, 106 through aperture 28, 68, 118. One contacts the tissues at a target surgical site with the increasingly protruding operative tip or surface 26, 66, 116 of head 16, 56, 106 and ultrasonically vibrates shaft 14, 54,114 and head 16, 56, 106 during contact of the operative tip or surface with the tissues. The induced vibrating of operative tip or surface 26, 66, 116 of head 16, 56, 106 against the target tissues subjects the same to cavitation and other mechano-acoustic loads which ablate or shave the tissues.

After ablation of target tissues at the operative site, instrument assembly 10, 50, 100 and particularly distal end portion 20, 60, 110 of sheath 18, 58, 108 are moved out of contact with the tissues at and adjacent to the surgical site, returning sheath distal end portion 20, 60, 110 to a neutral or rest position and retracting head 16, 56 at least partially into sheath 18, 58, 108 through aperture 28, 68, 118. The returning of distal end portion 20, 60, 110 of sheath 18, 58, 108 to the neutral or rest position occurs automatically owing to an internal spring action of flexible coupling or sheath portion 30, 70.

The surgical method preferably further includes feeding liquid 46, 92, 142 through aperture 28, 68, 118 during contact of the operative tip or surface 26, 66, 116 with the target tissues TT. The liquid may be fed out through distal opening 82, 132 as well as through gap 90, 140 in the embodiments of FIGS. 4-6 and 7-10.

Sheath 18, 58, 108 may be made of an integral piece of semi-rigid (e.g., polymeric) material that is sufficient flexible to allow limited deformation or bending in response to a laterally applied force F1, F2, F3. Alternatively, As discussed above, sheath 18, 58, 108 may incorporate different sections of different materials of different degrees of flexibility.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:
1. A surgical method comprising:
providing an ultrasonic surgical instrument assembly including a shaft with a head extending eccentrically to one side of said shaft, said instrument assembly further including a sheath surrounding said shaft and having a distal end portion with an aperture aligned with said head, said head being extendable through said aperture;

moving said instrument assembly so that said sheath comes into contact with tissues at an operative site;

pivotally deflecting said distal end portion of said sheath by virtue of a lateral pressure applied by the contact of said sheath with said tissues;

increasing a degree of protrusion of said head through said aperture by virtue of the deflecting of said distal end portion of said sheath;

contacting said tissues with an operative tip or surface of said head; and ultrasonically vibrating said shaft and said head during contact of said operative tip or surface with the tissues.

2. The method defined in claim 1, further comprising moving said instrument assembly to terminate contact between said tissues and said distal end portion of said sheath, returning said distal end portion to a neutral or rest position and retracting said head at least partially into said sheath through said aperture.

3. The method defined in claim 2 wherein the returning of said distal end portion to said neutral or rest position occurs automatically owing to an internal spring contact of a flexible coupling between said distal end portion and a base or hand piece of said instrument assembly.

4. The method defined in claim 1, further comprising feeding a liquid through said aperture during contact of said operative tip or surface with the tissues.

5. A surgical method comprising:

providing an ultrasonic surgical instrument assembly including a shaft with a head extending eccentrically to one side of said shaft, said instrument assembly further including a sheath surrounding said shaft and having a distal end portion with an aperture aligned with said head, said head being extendable through said aperture;

moving said instrument assembly so that said sheath comes into contact with tissues at an operative site;

pivotally deflecting said distal end portion of said sheath in response to a lateral pressure applied by the contact of said sheath with said tissues;

increasing a degree of protrusion of said head through said aperture by virtue of the deflecting of said distal end portion of said sheath;

contacting said tissues with an operative tip or surface of said head; and ultrasonically vibrating said shaft and said head during contact of said operative tip or surface with the tissues.

6. The method defined in claim 5, further comprising moving said instrument assembly to terminate contact between said tissues and said distal end portion of said sheath, returning said distal end portion to a neutral or rest position and retracting said head at least partially into said sheath through said aperture.

7. The method defined in claim 6 wherein the returning of said distal end portion to said neutral or rest position occurs automatically owing to an internal spring contact of a flexible coupling between said distal end portion and a base or hand piece of said instrument assembly.

8. The method defined in claim 5, further comprising feeding a liquid through said aperture during contact of said operative tip or surface with the tissues.

* * * * *